(12) United States Patent
Huang et al.

(10) Patent No.: US 9,163,054 B2
(45) Date of Patent: Oct. 20, 2015

(54) METHOD FOR F-18 FLT SYNTHESIS

(75) Inventors: Li-Yuan Huang, Taoyuan County (TW);
Yen-Hung Tu, Taoyuan County (TW);
Wen-Chin Su, Taoyuan County (TW);
Jenn-Tzong Chen, Taipei (TW);
Ting-Shien Duh, Taoyuan County (TW);
Wuu-Jyh Lin, Taoyuan County (TW)

(73) Assignee: INSTITUTE OF NUCLEAR ENERGY RESEARCH, ATOMIC ENERGY COUNCIL, Executive Yuan, R.O.C., Lungtan, Taoyuan (TW)

( * ) Notice: Subject to any disclaimer, the term of this patent is extended or adjusted under 35 U.S.C. 154(b) by 1065 days.

(21) Appl. No.: 13/237,067

(22) Filed: Sep. 20, 2011

(65) Prior Publication Data

US 2013/0072672 A1    Mar. 21, 2013

(51) Int. Cl.
*C07H 21/00* (2006.01)
*C07H 19/06* (2006.01)

(52) U.S. Cl.
CPC ..................................... *C07H 19/06* (2013.01)

(58) Field of Classification Search
CPC .. A61K 31/7072; C07H 19/06; C07H 19/073; C07H 5/02; C07H 21/00
See application file for complete search history.

(56) References Cited

U.S. PATENT DOCUMENTS 6,891,033 B2 *    5/2005    Martin et al. ................ 536/28.5

OTHER PUBLICATIONS

Seung Jun Oh et al. Fully automated synthesis system of 3'-deoxy-3'[18F]fluorothymidine, Nuclear Medicine and Biology, 31, 803-809, 2004.*
Sang Ju Lee et al. Simple and highly efficient synthesis of 3'-deoxy-3'[18F]fluorothymidine using nucleophilic fluorinaiton catalysed by protic solvent, Eur J Nucl Med Mole Imaging, 34, 1406-1409, 2007.*

* cited by examiner

*Primary Examiner* — Michael G Hartley
*Assistant Examiner* — Jagadishwar Samala
(74) *Attorney, Agent, or Firm* — Jackson IPG PLLC; Demian K. Jackson

(57) ABSTRACT

The present invention establishes a fast and simple [F-18] FLT synthesis process. Solid extraction units are used for purification to achieve an equally high and constant radiochemical yield and purity in a short period of time. By using a separation method, the impurities are reduced successfully while the total synthesis time is shortened. The radiochemical purity and the corrected radiochemical yield are both high.

8 Claims, 2 Drawing Sheets

METHOD FOR F-18 FLT SYNTHESIS

TECHNICAL FIELD OF THE INVENTION

The present invention relates to F-18 FLT synthesis; more particularly, relates to easily fabricating a contrast medium having fluorine(F)-18 ions with time saved and production increased.

DESCRIPTION OF THE RELATED ART

[$^{18}$F] 3'-deoxy-3'-fluorothymidine (FLT) is a thymidine analog developed for imaging of tumor proliferation through positron emission tomography (PET). It is an important drug used in the diagnosis of tumors. Currently, [F-18] FLT synthesis process takes approximately one hour to complete with specific devices through specific steps. But, the yield is still low generally. Hence, the prior art does not fulfill all users' requests on actual use.

SUMMARY OF THE INVENTION

The main purpose of the present invention is to easily fabricate a contrast medium having F-18 ions with time saved and production increased.

To achieve the above purpose, the present invention is a method for F-18 FLT synthesis, comprising steps of: (a) processing ion exchange with fluoride ions to obtain F-18 ions with coordination of an ion-exchange resin; (b) with coordination of tertiary butyl alcohol (TBA), washing out F-18 ions to be added with acetonitrile (ACN) and helium gas to process co-boiling; after cooling down to a room temperature, processing co-boiling again with ACN and helium gas; and cooling down to a room temperature; (c) obtaining reactant to be added with precursors to process fluoridation under a pressure; (d) adding HCl to the reactant to process hydrolysis by heating; (e) after cooling down the reactant, processing purification through solid extraction with coordination of water; (f) processing dilution and filtration to the reactant to obtain a product; and (g) putting the product into a product collecting trough, where the present invention uses a device comprising a pump controlling flowing of gas and fluid; a fluoride ion trough connected with the pump; an ion-exchange trough connected with the pump and the fluoride ion trough; a reaction trough, the reaction trough having a heater, connected with the pump and the ion-exchange trough; a feeding device connected with the pump and the reaction trough; a solid extraction tube connected with the pump and the reaction trough; a waste trough connected with the pump and the solid extraction tube; and a product collecting trough connected with the pump and the solid extraction tube. Accordingly, a novel method for F-18 FLT synthesis is obtained.

BRIEF DESCRIPTIONS OF THE DRAWINGS

Figure 1:
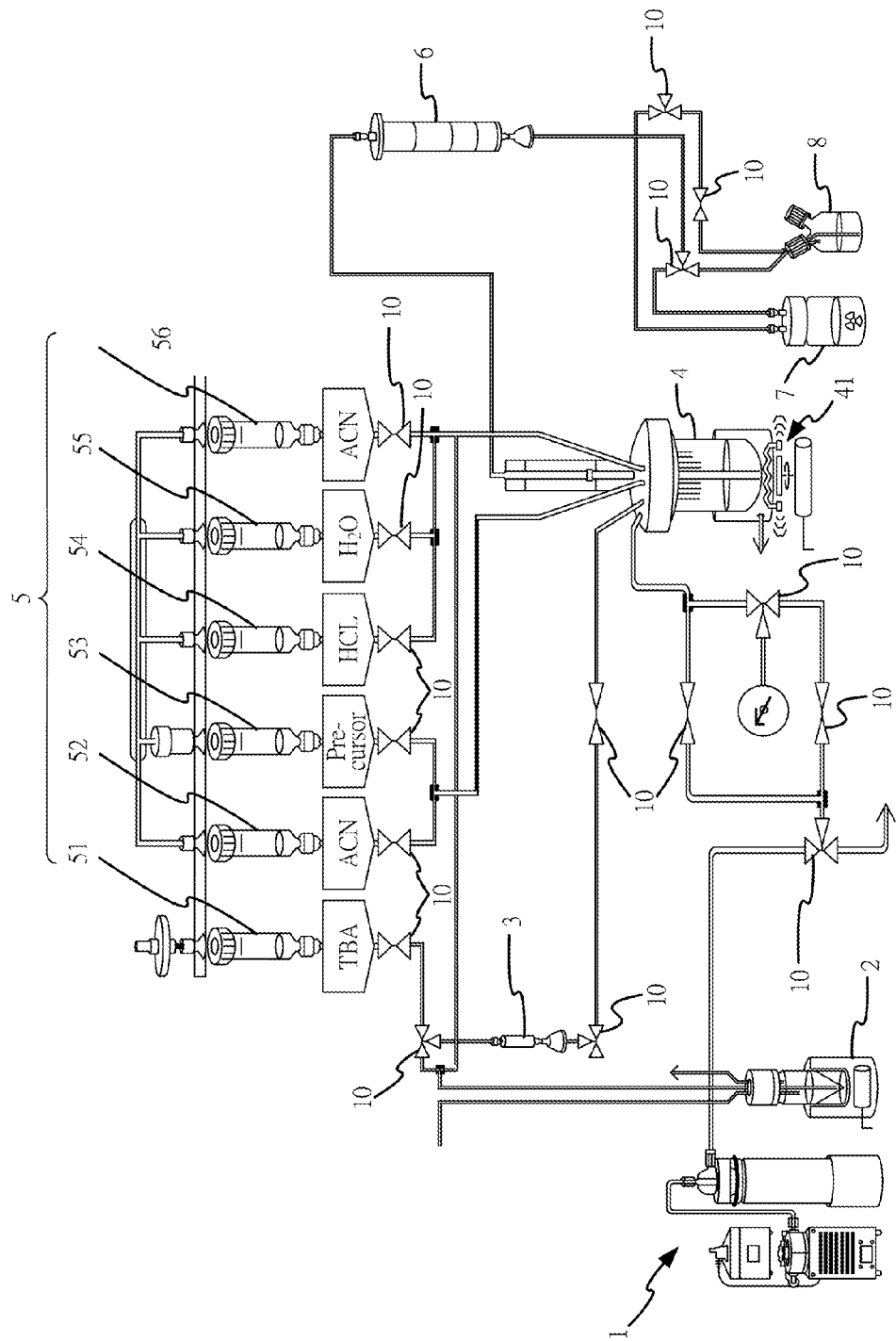
Figure 2:
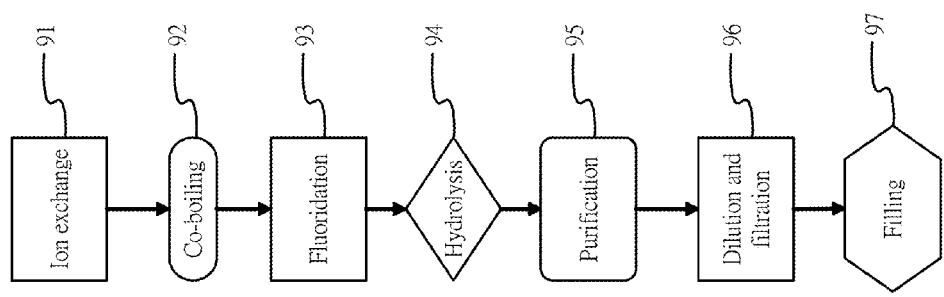

The present invention will be better understood from the following detailed description of the preferred embodiment according to the present invention, taken in conjunction with the accompanying drawings, in which FIG. 1 is the structural view showing the device used in the preferred embodiment according to the present invention; and FIG. 2 is the flow view showing the preferred embodiment.

DESCRIPTION OF THE PREFERRED EMBODIMENT

The following description of the preferred embodiment is provided to understand the features and the structures of the present invention.

Please refer to FIG. 1, which is a structural view showing a device used in the preferred embodiment according to the present invention. As shown in the figure, the present invention is a method for F-18 FLT synthesis. The device used for the present invention comprises a pump 1, a fluoride ion trough 2, an ion-exchange trough 3, a reaction trough 4, a feeding device 5, a solid extraction tube 6, a waste trough 7, and a product collecting trough 8, where a plurality of valves 10 are set between the pump 1, the fluoride ion trough 2, the ion-exchange trough 3, the reaction trough 4, the feeding device 5, the solid extraction tube 6, the waste trough 7 and the product collecting trough 8.

The pump 1 controls flowing of gas and fluid.

The fluoride ion trough 2 is connected with the pump 1.

The ion-exchange trough 3 is connected with the pump 1 and the fluoride ion trough 2.

The reaction trough 4 is connected with the pump 1 and the ion-exchange trough 3 and has a heater 41.

The feeding device 5 is connected with the pump 1 and the reaction trough 4 and comprises a first feeding tube 51, a second feeding tube 52, a third feeding tube 53, a fourth feeding tube 54, a fifth feeding tube 55 and a sixth feeding tube 56. Therein, the first feeding tube 51 is contained with tertiary butyl alcohol (TBA); the second feeding tube 52 is contained with acetonitrile (ACN); the third feeding tube 53 is contained with ACN and t-BuOH; the fourth feeding tube 54 is contained with HCl; the fifth feeding tube 55 is contained with water; and the sixth feeding tube 56 is contained with ACN.

The solid extraction tube 6 is connected with the pump 1 and the reaction trough 2 and is contained with PS–H+→C-18→Si→Al×2.

The waste trough 7 is connected with the pump 1 and the solid extraction tube 6.

The product collecting trough 8 is connected with the pump 1 and the solid extraction tube 6 and is contained with 10% NaCl and 0.2N NaOH in advance.

Please further refer to FIG. 2, which is a flow view showing the preferred embodiment. As shown in the figure, the present invention comprises the following steps:

(a) Ion exchange 91: Fluoride (F) ions in the fluoride ion trough 2 are guided into the ion-exchange trough 3 for processing ion exchange to generate F-18 ions with coordination of an ion-exchange resin.

(b) Co-boiling 92: With coordination of TBA obtained from the first feeding tube 51 for washing, F-18 ions are washed out to the reaction trough 4. ACN and helium gas obtained from the second feeding tube 52 are added for processing co-boiling with coordination of the heater 41 at a temperature of 75 Celsius degrees (° C.)~115° C. for a time period of 5 minute (min)~1 min. After the reactant is cooled down to a temperature of 70° C.~30° C., ACN and helium gas obtained from the sixth feeding tube 56 are added to the reactant in the reaction trough 4 for processing co-boiling again with coordination of the heater 41 at a temperature of 75° C.~115° C. for a time period of 5 min~1 min. Then, after the reactant is cooled down to a temperature of 70° C.~30° C., helium gas is stopped filling and the pump 1 is used for gas extraction for a time period of 5 min~1 min.

(c) Fluoridation 93: Precursors (ACN and t-BuOH) obtained from the third feeding tube 53 are added to the reactant in the reaction trough 4 to process fluoridation under a pressure with coordination of the heater 41 at a temperature of 130° C.~90° C. for a time period of 7 min~3 min. After the reactant is cooled down to a temperature of 105° C.~65° C., the pump 1 is used to simultaneously guide and extract gas for a time period of 5 min~1 min and then gas is further extracted for a time period of 5 min~1 min.

(d) Hydrolysis 94: HCl obtained from the fourth feeding tube 54 is added to the reactant in the reaction trough 4 to process hydrolysis by heating with coordination of the heater 41 at a temperature of 130° C.~90° C. for a time period of 7 min~3 min.

(e) Purification 95: The reactant obtained after hydrolysis is cooled down to a temperature of 70° C.~30° C. to be transferred to the solid extraction tube 6. Then, with PS–H+ →C–18→Si→Al×2 obtained from the solid extraction tube 6, purification is processed through solid extraction with coordination of water obtained from the fifth feeding tube, where waste solution obtained after the solid extraction is drained into the waste trough 7.

(f) Dilution and filtration 96: The extracted material is diluted with water obtained from the fifth feeding tube 55 added with 30%~10% of NaCl; and, then, is filtered through a sterile membrane having 0.22 μm millipores to obtain a product.

(g) Filling 97: At last, the product is put into the product collecting trough 8. The product collecting trough 8 is a sterile vial and is contained with 10% NaCl and 0.2N NaOH in advance for later dispensing.

To sum up, the present invention is a method for F-18 FLT synthesis, where a contrast medium having F-18 ions is fabricated easily with time saved and production increased.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method for F-18 FLT synthesis, comprising steps of:
   (a) processing ion exchange with fluoride ions to obtain fluorine(F)-18 ions with coordination of an ion-exchange resin;
   (b) with coordination of tertiary butyl alcohol (TBA), obtaining F-18 ions to be added with acetonitrile (ACN) and helium gas to process co-boiling; wherein said co-boiling process is processed at a temperature of 75° C.~150° C. for a time period of 5 minute (min)~1 min after cooling down to a room temperature, processing co-boiling again with ACN and helium gas; and cooling down to a room temperature;
   (c) obtaining reactant to be added with ACN and t-BuOH to process fluoridation under a pressure;
   (d) adding HCl to said reactant to process hydrolysis by heating;
   (e) after cooling down said reactant, processing purification through solid extraction with coordination of water;
   (f) processing dilution and filtration to said reactant to obtain a product; and
   (g) putting said product into a product collecting trough.

2. The method according to claim 1, wherein, in step (b), said reactant is cooled down to a temperature of 70° C.~30° C.

3. The method according to claim 1, wherein, in step (b), said reactant is cooled down to temperature of 70° C.~30° C. after co-boiling again; and, then, said helium gas is shut off for a time period of 5 min~1 min to process gas extraction.

4. The method according to claim 1, wherein, in step (c), said reactant is pressed at a temperature of 130° C.~90° C. for a time period of 7 min~3 min; then said reactant is cooled down to a temperature of 105° C.~65° C. and gas is guided and extracted for a time period of 5 min~1 min at the same time; and, then, gas is further extracted for a time period of 5 min~1 min.

5. The method according to claim 1, wherein, in step (d), said reactant is heated at a temperature of 130° C.~90° C. for a time period of 7 min~3 min.

6. The method according to claim 1, wherein, in step (e), said reactant is cooled down to a temperature of 70° C.~30° C. after processing hydrolysis.

7. The method according to claim 1, wherein, in step (f), said dilution is processed by a water solution having 30%~10% NaCl; and said filtration is processed with a sterile membrane having 0.22 μm millipores to obtain said product.

8. The method according to claim 1, wherein, in step (g), said product collecting trough is a sterile vial and is contained with 10% NaCl and 0.2N NaOH in advance.

\* \* \* \* \*